US006490335B1

(12) United States Patent
Wang et al.

(10) Patent No.: US 6,490,335 B1
(45) Date of Patent: Dec. 3, 2002

(54) HELICAL SEGMENT IMAGE RECONSTRUCTION

(75) Inventors: Sharon Xiaorong Wang, Brookfield, WI (US); Brian Grekowicz, Pewaukee, WI (US)

(73) Assignee: GE Medical Systems Global Technologies Company LLC, Waukesha, WI (US)

( * ) Notice: Subject to any disclaimer, the term of this patent is extended or adjusted under 35 U.S.C. 154(b) by 0 days.

(21) Appl. No.: 09/990,423

(22) Filed: Nov. 21, 2001

(51) Int. Cl.[7] .................................................. A61B 6/03
(52) U.S. Cl. .............................. 378/15; 378/4; 378/901; 382/131
(58) Field of Search .............................. 378/4, 15, 19, 378/901; 382/131

(56) References Cited

U.S. PATENT DOCUMENTS

| | | | | |
|---|---|---|---|---|
| 5,291,402 A | * | 3/1994 | Pfoh ............................ | 378/13 |
| 5,377,250 A | * | 12/1994 | Hu ............................... | 378/15 |
| 5,430,783 A | * | 7/1995 | Hu et al. ...................... | 378/15 |
| 6,339,632 B1 | * | 1/2002 | Besson ......................... | 378/15 |
| 6,404,842 B1 | * | 6/2002 | Hsieh ........................... | 378/15 |
| 6,418,184 B1 | * | 7/2002 | Wang et al. .................. | 378/15 |

\* cited by examiner

*Primary Examiner*—Drew A. Dunn
(74) *Attorney, Agent, or Firm*—Quarles & Brady, LLP; Carl Horton

(57) ABSTRACT

A method and apparatus for performing image reconstruction using data obtained by an N beam helical scan, the method including generating projection data arrays for each of the N rows in a CT detector, weighting the data arrays using a unique weighting function that including different weighting functions for a first detector row, a last detector row and the middle detector rows between the first and last detector rows thereby generating helical weighted arrays for each row, applying a half scan weight to each helical weighted array and using the half scan weighted arrays to generate a slice image.

20 Claims, 7 Drawing Sheets

HELICAL SEGMENT IMAGE RECONSTRUCTION

STATEMENT REGARDING FEDERALLY SPONSORED RESEARCH

Not applicable.

CROSS-REFERENCE TO RELATED APPLICATIONS

Not applicable.

CROSS-REFERENCE TO RELATED APPLICATIONS

Not applicable.

BACKGROUND OF THE INVENTION

The present invention relates to multi-slice helical computerized tomography and more particularly to an algorithm, method and apparatus for using the same which increase the quality of resulting images by employing a new weighting algorithm.

In computerized tomography (CT) X-ray photon rays are directed through a region of interest (ROI within a patient toward a detector. Attenuated rays are detected by the detector, the amount of attenuation indicative of the make up (e.g. bone, flesh, air pocket, etc.) of the ROI through which the rays traversed. The attenuation data is then processed and back-projected according to a reconstruction algorithm to generate an image of the patient's internal anatomy. Generally, the "back projection" is performed in software but, as the name implies, is akin to physically projecting rays from many different angles within an image plane through the image plane, the values of rays passing through the same image voxels being combined in some manner to have a combined effect on the voxel in the resulting image. Hereinafter the data corresponding to rays which are back projected will be referred to as back projection rays.

During data acquisition, if a patient moves, artifacts can occur in the resulting image which often render images useless or difficult to use for diagnostics purposes. For this and other reasons, as in other imaging techniques, the CT industry is constantly trying to identify ways to reduce the duration of acquisition periods without reducing the quality of the data acquired.

In addition, because huge amounts of data are acquired during an acquisition period and the processing methods for image reconstruction from the gathered data are relatively complex, a huge number of calculations are required to process data and reconstruct an image. Because of the huge number of required calculations, the time required to process collected data and reconstruct an image is appreciable. For this reason the CT industry is also constantly searching for new processing methods and algorithms which can speed up the reconstruction process.

Various CT system features and procedures have been developed to increase data acquisition speed and to speed up the reconstruction process. Some of the more popular features and procedures including fan beam acquisition, simultaneous multiple slice acquisition, helical scanning and half-scanning. In fan beam acquisition the source is collimated into a thin fan beam which is directed at a detector on a side opposite a patient. In this manner, a complete fan beam projection data set is instantaneously generated for a beam angle defined by a central ray of the source fan beam. The source and detector are rotated about an image plane to collect data from all (e.g., typically 360 degrees) beam angles. Thereafter the collected data is used to reconstruct an image in the image plane. Thus, fan beam acquisition reduces acquisition period duration.

With respect to half-scanning, assuming a patient remains still during a data acquisition period, conjugate data acquisitions (i.e., data acquired along the same path from opposite directions) should be identical. In addition, using a fan beam, at least one ray can be directed through an image plane from every possible beam angle without having to perform a complete rotation about the patient.

For example, referring to FIG. 3, an annular gantry opening 70 is illustrated with a patient slice 42 disposed (support table not illustrated) therein and with respect to a Cartesian coordinate system where the Z-axis is into the Figure and defines a transport axis. A source 10 is illustrated in first, second, third and fourth positions as 90, 90', 90" and 90''', respectively. When in the first position, source 10 generates a fan beam 40 which includes a central ray Rc and additional rays diverging therefrom along fan angles, the maximum fan angle being G. The beam angle $\beta$ is defined as the angle formed by central ray Rc with respect to the vertical Y-axis.

When in the fourth position, source 10 generates a fan beam 40''' which also includes a central ray (not illustrated) and rays diverging therefrom to form the fan beam. By rotating the source from the first to the fourth position in a clockwise direction data is collected at least once from every possible beam angle through slice 42 (i.e., the image plane). As known in the industry, data corresponding to every beam angle corresponding to a single image plane can be collected after a $(\pi+2\Gamma)2\pi$ rotation about the patient. Because less than an entire rotation about the image plane is required to acquire the imaging data these acquisition methods and systems are generally referred to as partial-scan methods and systems and, more specifically, where data is collected during a minimal gantry rotation, the methods and systems are referred to as half-scan methods and systems. Thus, half-scan acquisition has been employed to reduce acquisition period duration in conjunction with single row detectors.

In addition, because relatively less data has to be processed in the case of half-scan imaging methods and systems to generate an image, half-scan methods and systems also have the advantage of potentially reducing data processing and reconstruction times.

As a result of the fan beam geometry of the x-ray source and the detector array, a half scan contains certain redundant data. This redundant data requires that the half scan data set be weighted with a "half scan weighting" function so that the redundant data does not make a disproportionate contribution to the final image when incorporated with the non-redundant data. The weighting and reconstruction of images from a half scan data set are discussed in detail in "Optimal Short Scan Convolution Reconstruction for Fanbeam CT", Dennis L. Parker, Medical Physics 9(2) March/April 1982.

While fan beams and half-scans have several advantages, often, during a diagnostics exercise a system user typically will not know the precise location within a patient of an object, cavity, etc. of interest to be imaged. For this reason, it is advantageous for a system user to be able to generate several cross sectional images in rapid succession by selecting different image/reconstruction planes. In these cases rapid data processing is extremely important to minimize delays between image generation so that a user does not lose her train of thought between image views.

Single slice detectors, fan beams and half-scans can be used to generate data in several different parallel image planes which, after data acquisition, can be used by a processor to generate an image anywhere between the image planes through interpolation/extrapolation procedures known in the art. For example, assume that during two data acquisition periods first and second data sets were acquired which correspond to first and second parallel acquisition planes, respectively, the planes separated by 0.25 inches. If a user selects an image plane for reconstructing an image which resides between the first and second acquisition planes, interpolation between data in the first and second sets can be used to estimate values of data corresponding to the selected image plane. For instance, assume that, among other rays, during the acquisition periods a first ray and a second ray were used to generate data in the first and second sets, respectively, and that the first and second rays were parallel (i.e. had the same beam and fan angles). In this case, by interpolating between the data acquired from the first and second rays generates an estimated value corresponding to a hypothetical back projection ray which is parallel to the first and second rays and which is within the image plane. By performing such interpolation to generate back projection rays for every beam and fan angle through the image plane a complete data set corresponding to the image plane is generated.

While such systems work, unfortunately, the acquisition time required to generate data corresponding to many image planes is excessive and inevitable patient movement often causes image artifacts.

One way to speed up data acquisition corresponding to several image planes is by employing a multi-row detector with a fan beam. In multi-row detector systems, a relatively thick fan beam is collimated and directed at a multi-row detector with a patient there between, each detector row in effect gathering data for a separate "slice" of the thick fan beam along the Z or translation axis perpendicular to a fan beam width.

After data acquisition an interface enables a system user to select an image plane from within the area corresponding to the collected data. The selected image plane is between the row centers of at least two adjacent detector rows. After image plane selection, a processor interpolates between data corresponding to adjacent rows to generate back projection rays corresponding to the selected image plane. When another image corresponding to a different image plane is desired, after selecting the plane, the processor again identifies an acquired data subset for interpolation, additional processing and back projection. Thus, multi-row detector systems further reduce data acquisition period duration where several image planes may be selected for reconstruction.

One limitation with multi-row detectors is that, during a single acquisition period, data can only be collected which corresponds to the detector thickness. To collect additional data corresponding to a greater patient volume, after one acquisition period corresponding to a first volume, the patient has to be moved along a translation axis until a second volume which is adjacent the first volume is between the source and detector. Thereafter a second acquisition process has to be performed. Similarly, to collect additional data corresponding to a third volume the patient has to be transported to another relative location with respect to the source and detector. Required translation without acquisition necessarily prolong the acquisition period and the additional acquisition time and aligning processes inevitably result in relative discomfort, additional patient movements and undesirable image artifacts.

Helical scanning systems have been developed so that data can be collected during a single acquisition period without halting patient translation during the acquisition period. In a helical scanning system, the source and detector array are mounted on opposing surfaces of an annular gantry and are rotated there around as a patient is transported at constant speed through the gantry. The X-ray beam sweeps a helical path through the patient, hence the nomenclature "helical scanning system". Data acquisition can be sped up by increasing operating pitch (i.e., table translation speed relative to gantry rotation rate).

Various combinations of the fan-beam, multi-slice, half-scan and helical scanning features have been combined to realize synergies and have been somewhat successful. For example, one system combines a multi-row fan beam detector and a fan beam source with a helical scanning procedure to rapidly acquire imaging data using a high pitch/high speed mode.

After high pitch helical data is acquired, the data is processed to generate back projection ray estimates and account for data nuances that are caused by the helical acquisition. The data processing typically includes application of a helical weighting function to the "views" (i.e., the data collected bat a specific gantry angle $\beta$) collected by each detector row and then addition of the weighted views corresponding to identical gantry angles $\beta$. The helical weighting functions are typically gantry angle $\beta$ dependent. For instance, one exemplary helical weighting function is triangular having a value of one at a central gantry angle $\beta$ that is aligned with a selected imaging plane and tapering off to zero at $\beta$ angles on both sides of the central $\beta$ angle corresponding to half the Z-axis distance between adjacent detector row center points. Thus, the helical weighting functions overlap. Rules are enforced such that the summation of the helical weighting function for all rows at a specific gantry angle $\beta$ is one. Generally, after helical weights are applied, a weighted view from each side of a selected imaging plane are added to generate data corresponding to the imaging plane and a specific gantry angle $\beta$.

Referring again to FIG. 3, in these high speed helical scanning systems, during acquisition data is acquired with source 10 at position 90, the source and detector are rotated (while data is collected) about gantry opening 70 as the patient 42 is transported there through. A processor collects data during transport and rotation from many different beam and fan angles. After source 10 rotates through a complete rotation and reaches position 90 again, additional data is gathered at that position. Because the patient 42 is transported along the Z axis during acquisition, while source 10 is at the same location 90 relative to opening 70 at the beginning and at the end of the rotation, the source and data collected are at a different Z location relative to patient 42. Hereinafter data collected for the same beam and fan angles but at different Z locations will be referred to as consecutively collected data.

To generate a slice image at a specific image plane, many interpolation techniques interpolate between consecutively collected data (i.e., data from source 10 at the same beam angle (e.g., position 90 in FIG. 3) and fan angle but at different Z (i.e., translation axis) locations). In other words, many interpolation techniques require data from more than a single source rotation to generate an image. In addition, because data from more than one rotation is required to interpolate, the data collection is relatively large and processing and reconstruction period durations are excessive. Moreover, where interpolation is between consecutively collected data, the resulting image has a "thickness" characteristic which corresponds to a relatively thick patient volume which is unsuitable or at least not optimal for many diagnostic purposes.

Instead of using only interpolation to generate a slice image from a helical data set, some algorithms use data from a single half scan data set using interpolation at gantry angles where there is sufficient data to support interpolation and use extrapolation techniques at gantry angles where there is insufficient data to support interpolation. For instance, one such algorithm is described in U.S. Pat. No. 6,301,325 which issued on Oct. 9, 2001 and is entitled "Half-Scan Algorithm for use with a High Speed Multi-Row Fan Beam Helical Detector" and is commonly owned with the present invention.

Unfortunately there are several problems with extrapolation based algorithms. First, ideally only "bounded" data is used to generate an image where the term "bounded" is used to refer to data corresponding to views within a half scan gantry angle range $\Delta\beta$. By limiting data used to generate an image to bounded data, generally, more accurate images that are true to the anatomical structures they purport to represent, are generated. Extrapolation is clearly an unbound process.

Second, extrapolation processes require additional views corresponding to the second and second to last detector rows (i.e., in an eight row detector the second and seventh detector rows) which complicate the computation process appreciably. To this end, extrapolation typically takes place at the ends of a half scan data range and requires helical weighting functions corresponding to the second row and the second to last row in each detector array to be extended and applied to additional views outside the normal weighting function range. For instance, in the case of an eight row detector, views collected by the seventh row are used for three purposes. First, some of the seventh row views are interpolated with sixth row views to generate interpolated views within the image plane for a sub-set of gantry angles. Second, some of the seventh row views are interpolated with eighth row views to generate interpolated views within the image plane for another subset of gantry angles. Third, additional seventh row views have to be extrapolated in conjunction with eighth row views to generate the extrapolated views required to generate an image. In addition to requiring additional calculations to apply weights to the additional row views, calculations are further complicated as special extended weighting functions have to be developed and applied by a processor.

For the reasons discussed above neither interpolation between data corresponding to more than one gantry rotation or extrapolation are optimal and therefore it would be advantageous to have an image generating algorithm that is computationally simple and accurate and that provides high quality images using a single half scan data set.

SUMMARY OF THE INVENTION

It has been recognized that different helical weighting functions can be applied to views corresponding to end detector rows in a multi-row CT detector and that a standard weighting function can be applied to each of the views corresponding to detector rows between the first and last rows (i.e., from the second to the second last row) to generate high quality images where the views used to generate the slice image correspond to a single half scan data acquisition. Importantly, using the inventive algorithm, interpolation between data from more than one gantry revolution is not necessary and extrapolation past bound data or row views can be avoided.

More specifically, where portions of helical weighting functions corresponding to adjacent detector rows overlap and therefore each helical function corresponding to an end detector row overlaps an adjacent helical function, the non-overlapping portions of each helical weighting function corresponding to each end detector row are set equal to one. After the helical weighting functions are applied to the row views, half scan weighting functions are then applied and relatively accurate images result.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DESCRIPTION OF THE PREFERRED EMBODIMENT

A. Hardware

Figure 1:
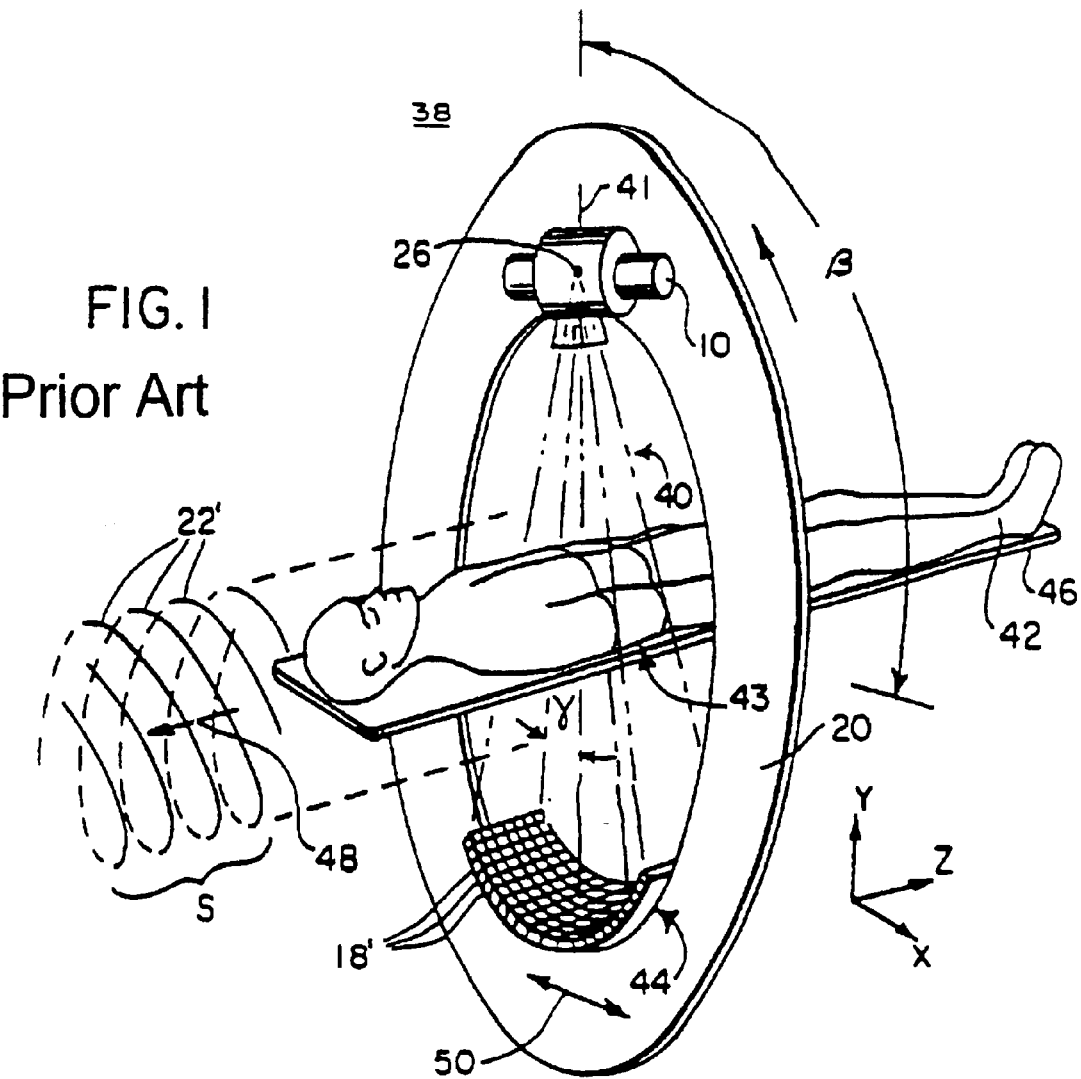
FIG. 1 is a perspective view of a CT apparatus used to practice the present invention which includes a detector array having rows and columns of detector elements and fan beam source.

Referring now to FIG. 1, a CT scanner for use with the present invention includes a gantry 20 having an opening (i.e., defining an imaging area) supporting an x-ray source 10 oriented to project a fan beam 40 of x-rays along the beam axis 41 through a patient 42 to a supported and opposed detector array 44. The gantry 20 rotates to swing the beam axis within a gantry plane 38 defining the x–y plane of a Cartesian coordinate system. Rotation of the gantry 20 is measured by beam angle $\beta$ from an arbitrary reference position within the gantry plane 38.

A patient 42 resets on a table 46 which may be moved along a translation axis 48 aligned with the Z-axis of the Cartesian coordinate system. Table 46 crosses gantry plane 38 and is radio-translucent so as not to interfere with the imaging process.

Figure 3:
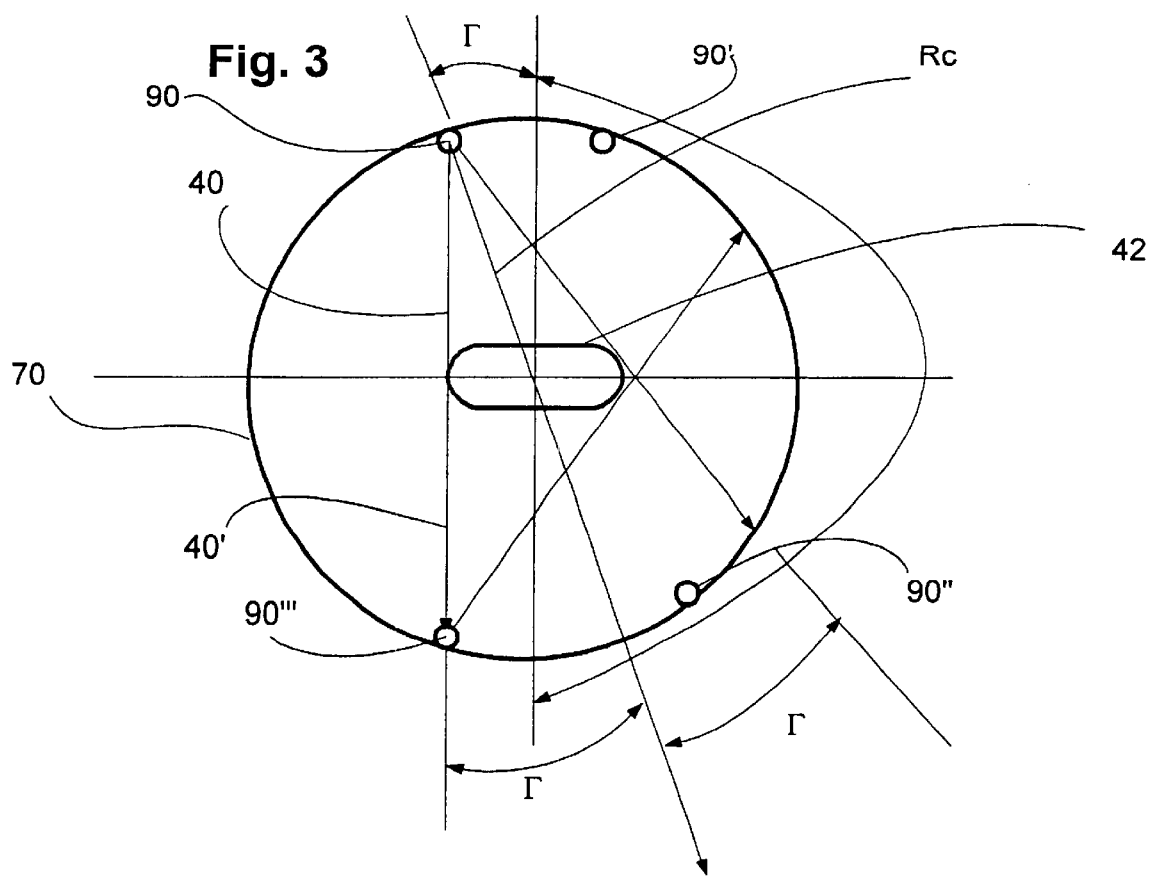
FIG. 3 is a schematic view illustrating a gantry opening with a radiation source positioned at different locations with respect to the opening and also illustrating fan beams which correspond to the beginning and end source positions of an exemplary half-scan.

The x-rays of the fan beam 40 diverge from the beam axis 41 within the gantry plane 38 across a transverse axis 50 generally orthogonal to both the beam axis 41 and the translation axis 48 at a fan beam angle γ. Referring also to FIG. 3, the x-rays of beam 40 also diverge slightly from the beam axis 41 and the gantry plane 38 across the Z-axis 48. A maximum beam angle γ is identified hereinafter by symbol Γ.

After passing through patient 42, the x-rays of the fan beam 40 are received by detector array 44 which includes a plurality of detector elements 18'. Referring also to FIG. 3, detector elements 18' in exemplary array 44 are arranged in eight rows R1 through R8 (i.e., array 44 is an eight slice detector) extending along the traverse axis 50 that subdivide array 44 along the Z-axis and a plurality of columns extending along Z-axis 48. The width W of detector array 44 is measured along Z-axis 48. The surface of detector array 44 may be planar or may follow a section of a sphere or cylinder having a center at focal spot 26 or alternatively at the system isocenter.

The detector elements 18' each receive x-rays and provide intensity measurements along separate rays of the fan beam 40. Each intensity measurement describes the attenuation via a line integral of one fan beam ray passing through a portion of volume 43 of patient 42. The dimension of volume 43 along Z-axis 48 is greater than the Z-axis width of eight slice array 44.

Figure 2:
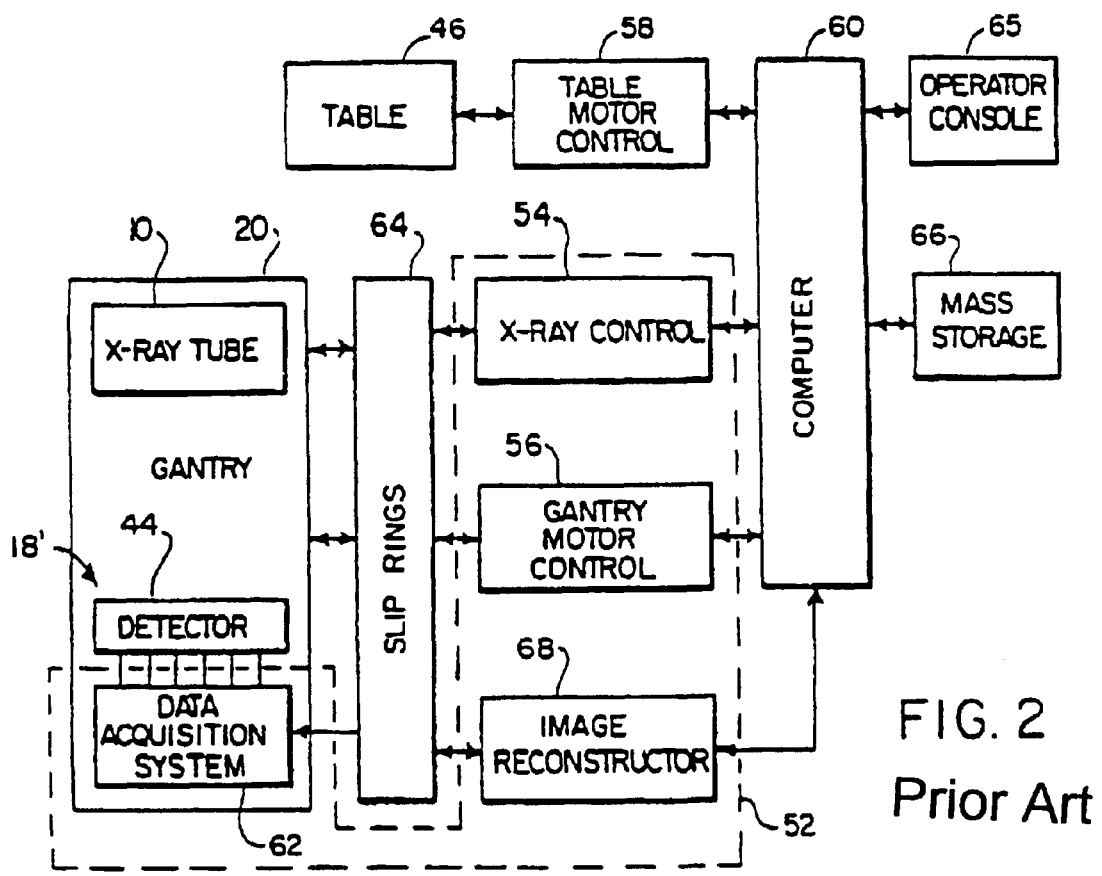
FIG. 2 is a block diagram of CT control system which may be used to control the CT apparatus of FIG. 1 and which is useful for the purposes of practicing the present invention.

Referring to FIGS. 1 and 2, an exemplary control system for controlling the CT imaging system of FIG. 1 includes gantry associated control modules collectively identified by numeral 52, a table motor control 58, slip rings 64, a central processing computer 60, an operator's console 65 and a mass storage device 66. Modules 52 include an x-ray control 54, a gantry motor control 56, a data acquisition system 62 and an image reconstructor 68. X-ray control 54 provides power and timing signals to the x-ray source 10 to turn it on and off as required under the control of a computer 60. Gantry motor control 56 controls the rotational speed and position of the gantry 20 and provides information to computer 60 regarding gantry position. Data acquisition system 62 samples and digitizes intensity signals from the detector elements 18' of detector array 44 provides the digitized signals in the form of helical data row views to computer 60 for storage in mass storage device 66. Reconstructor 68 is linked to computer 60 for receiving data there from and weighting the data according to the inventive method, filtering the weighted data and back-projecting the data to, as its label implies, construct a slice image for viewing.

Each of the above modules is connected to associated gantry mounted components via slip rings 64 and is also linked to computer 60 for control purposes Slip rings 64 permit gantry 20 to rotate continuously through angles greater than 360° to acquire projection data.

The speed and position of table 46 along translation axis 48 is controlled by computer 60 by means of table motor control 58. Computer 60 receives commands and scanning parameters via operator console 65 that generally includes some type of visual interface device (e.g., a CRT display) and one or more input devices (e.g., a keyboard, a mouse controlled display cursor, etc.). Console 65 allows an operator to enter parameters for controlling a data acquiring scan and to display constructed image and other information from computer 60.

Mass storage device or memory 66 provides a means for storing operating programs for the CT imaging system, as well as image data for future reference by the operator. Both computer 60 and the image reconstructor 68 have associated electronic memory (not shown) for storing data and pulse sequencing programs.

In operation, gantry motor control 56 brings gantry 20 up to a rotational speed and table motor control 58 begins translation of table 46 along translation axis 48. The x-ray control 54 turns on x-ray source 10 and projection data is acquired on a continuous basis. The table 46 translation speed relative to the gantry rotation rate is referred to as the operating "pitch". At each beam angle B, the projection data acquired comprises intensity signals corresponding to each detector element 18' at each particular column and row of array 44. The collected data is stored in storage device 66 as helical data including row views correlated to gantry angles.

Referring again to FIG. 3, the eight rows R1–R8 of detectors 44 define in an eight fan beam system. The x-ray fan beam 40 is, in effect, split into eight fan beams displaced along the Z-axis.

Referring now to FIGS. 1 through 3 and FIG. 7, image reconstructor 68 includes a summer 118, a filter and back-projector 116 and separate processing circuitry assemblies for each of the detector rows R1 through R8, the separate assemblies identified by labels 100(R1) through 100(R8), respectively. Each of assemblies 100(R1) through 100(R8) is essentially identical and operates in a similar fashion and therefore, in the interest of simplifying this explanation, only circuitry assembly 100(R1) is explained here in detail. It should suffice to say here that assembly 100(R1) processes data row views generated by row R1 of detector array 44, assembly 100(R2) processes data row views generated by row R2 of array 44, and so on, and that array output signals of assemblies 100(R) through 100(R8) are provided to summer 118 which adds the array signals to generate weighting data views within a selected slice image plane that can be filtered and back-projected to generate an image corresponding to the image plane.

Figure 7:
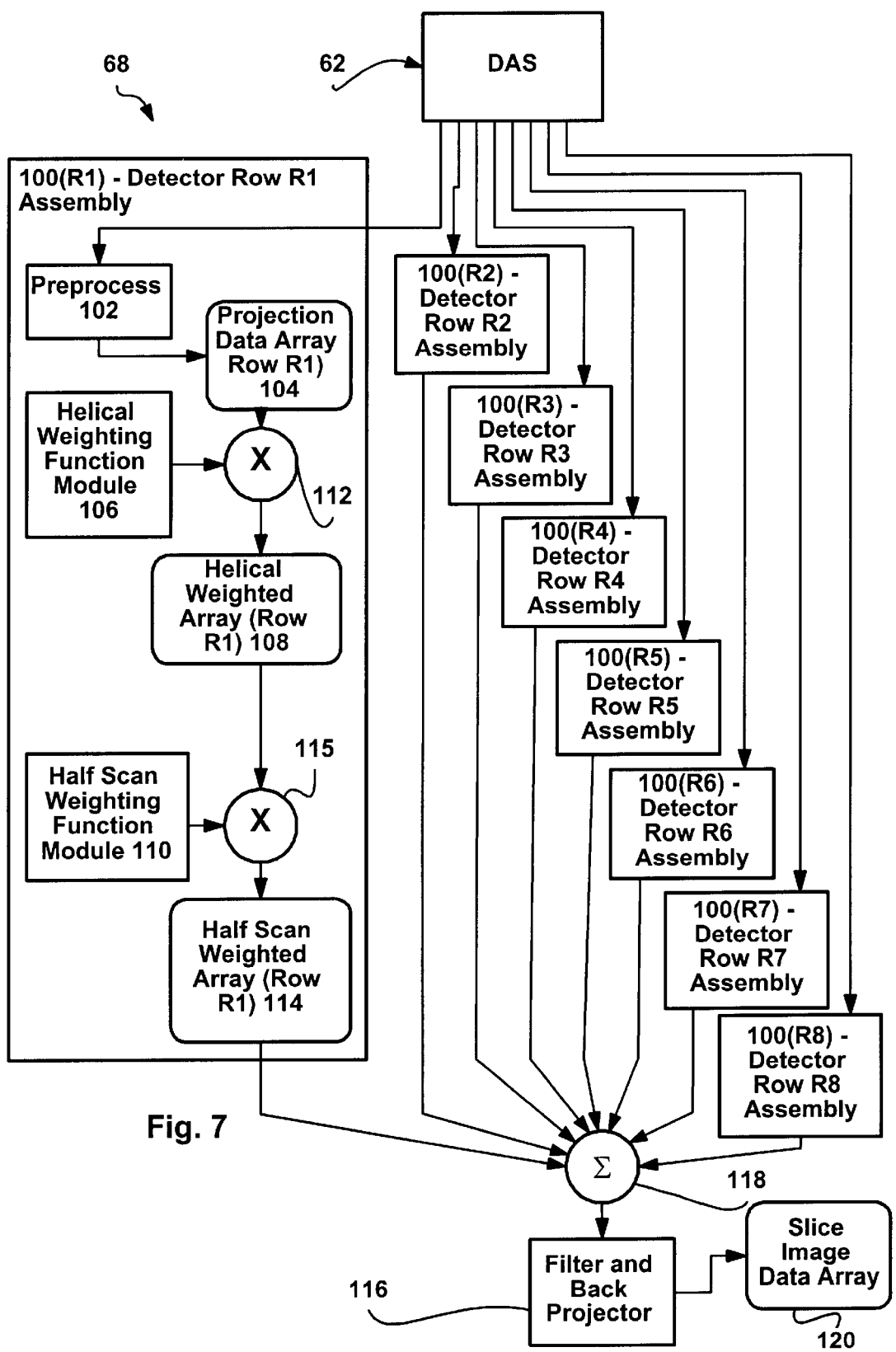
FIG. 7 is a schematic diagram illustrating an exemplary image reconstructor according to the present invention.

Referring to assembly 100(R1), assembly 100(R1) includes a preprocessor 102, first and second multipliers 112 and 115, respectively, a helical weighting function module 106 and a half scan weighting function module 110. Assembly 100(R1) components receive row views corresponding to detector row R1 and alter the received views several times to generate intermediate data arrays, the end result being a half scan weighted array 114 corresponding to row R1. In FIG. 7, to distinguish data arrays from assembly 100(R1) components, the arrays are identified by blocks having rounded edges while assembly components are identified by blocks having sharp angles. The intermediate arrays include a projection data array 104 and a helical weighted array 108.

Referring still to FIGS. 2 and 7, each row view of data from DAS 62 corresponding to detector row R1 is provided to preprocessor 102 where the view data is preprocessed to correct for various well-known errors such as beam hardening, offsets and variations in detector and channel gain. In addition, preprocessor 102 generates the negative logarithm of the view to provide projection data which is stored as the projection data array 104.

The projection data array 104 is read out and the helical weighting function generated by module 106 is applied to the projection data array 104 by multiplier 112 thereby generating the helical weighted array 108 which is again stored. The helical weighted array 108 is read out and the half scan weighting function generated by module 110 is applied to the helical weighted array 108 by multiplier 115 thereby generating the half scan weighted array 114 which is once again stored.

The half scan weighted array 114 is provided to summer 118 along with similar arrays from assemblies 100(R2)

through 100(R8). The arrays are summed by summer 118 to generate a combined slice plane data array. The combined array is provided to filter-back-projector 116 which filters and back-projects the combined array views to produce the slice image 120. The resulting slice image array 120 is stored in device 66 for later use or may be displayed to the operator via console 65.

In the alternative, instead of summing the half scan weighted arrays prior to filtering and back-projecting, each half scan weighted array may be separately filtered and back-projected to generate separate image data arrays for each row. Thereafter, the separate image data arrays may be summed on a pixel-by-pixel basis to generate the combined and final slice image array 120.

B. Weighting Processes

The present invention, in one form, relates specifically to the creation of weighted projection data arrays 108. In this regard, an inventive method generally includes two separate sub-processes including a helical weighting process and a half scan weighting process. These two processes will be described sequentially. With respect to the following discussion, label d denotes the detector row spacing measured (i.e., the z-axis spacing) at the axis of gantry rotation 48, s denotes the table feeding speed per gantry rotation, and pitch p denotes the ratio of d and s such that:

$$p = s/d. \qquad \text{Eq. 1}$$

1. Helical Weighting Process

Figure 4:
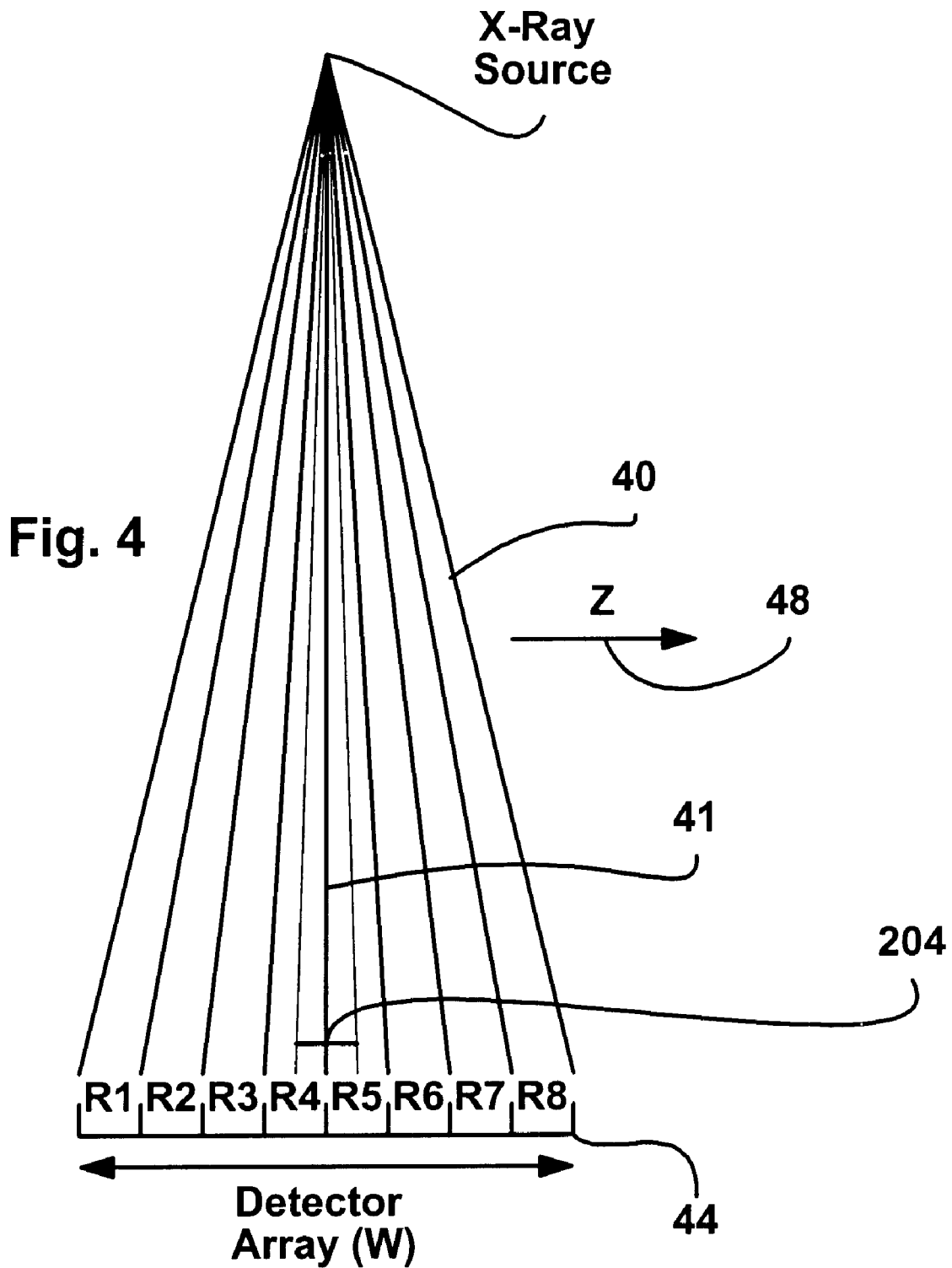
FIG. 4 is a schematic diagram illustrating an X-ray source and an eight row detector that divides the source beam into eight separate radiation beams.
Figure 5:
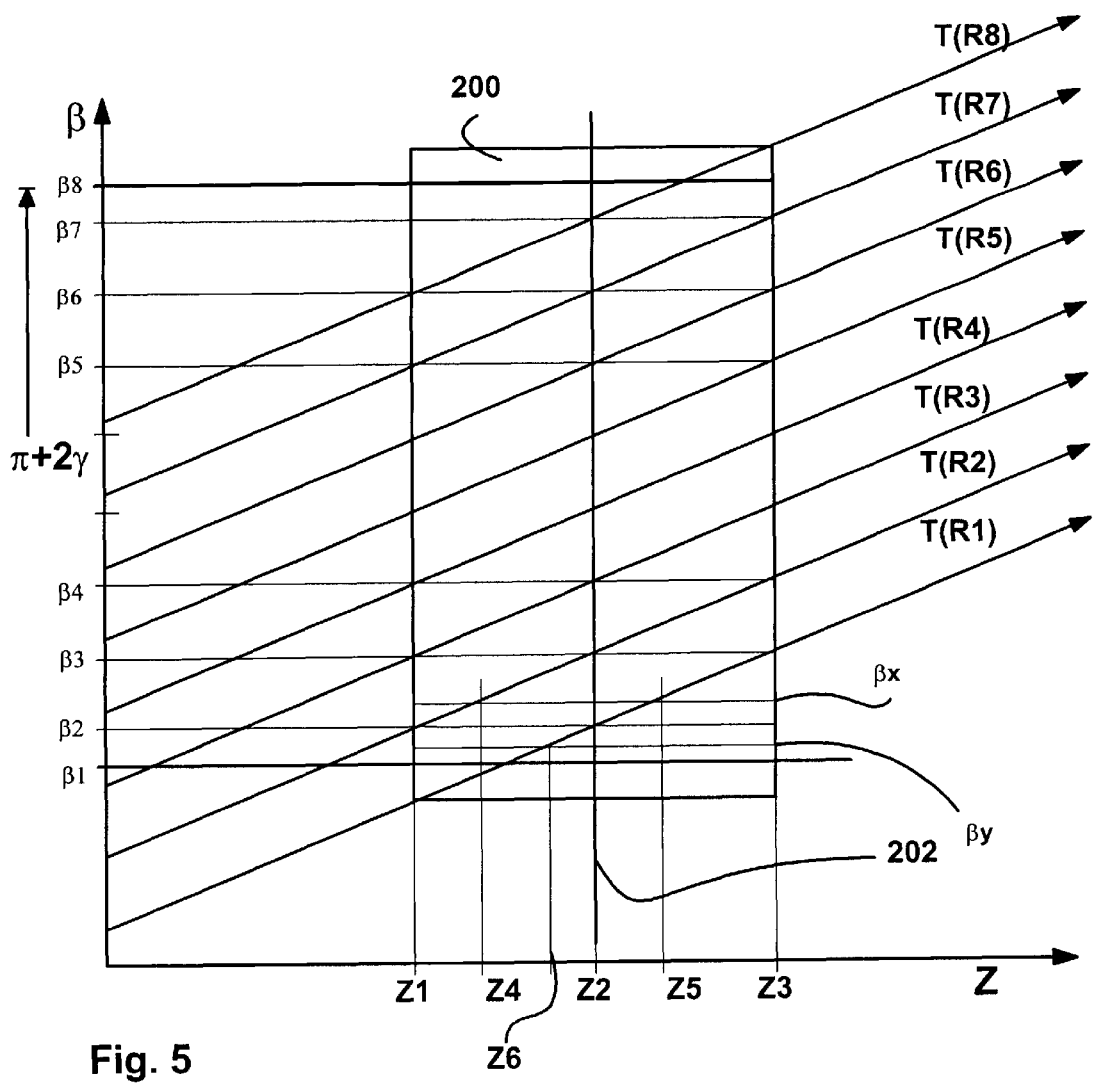
FIG. 5 is a schematic diagram illustrating detector view trajectories for an eight row CT detector and the relationship between the views and weighting functions illustrated in more detail in FIG. 6.

Referring now to FIG. 5, trajectories T(R1) through T(R8) of views defined by detector rows R1 through R8, respectively, during a helical data acquisition process are illustrated where trajectories are plotted as gantry angles (i.e., the angle defined by a central source ray (e.g., see ray 41 in FIG. 4) relative to Z-axis location of corresponding rows. For instance, referring specifically to trajectory T(R2), when the gantry angle (i.e., the angle defined by ray 41 in FIG. 4) is at angle β2, the view defined by trajectory T(R2) corresponding to row R2 is aligned with Z-axis location Z1 as illustrated. Similarly, when the gantry angle is at β3, the view defined by trajectory T(R2) corresponding to row R2 is aligned with Z-axis location Z2 and when the gantry angle is at β4, the view defined by trajectory T(R2) corresponding to row R2 is aligned with Z-axis location Z3 as illustrated. Between gantry angles β2 and β4 row R2, and hence view trajectory T(R2), is aligned with Z-axis locations between Z1 and Z3.

Referring still to FIG. 5, line 202 is a Z-axis plane of reconstruction corresponding to a slice image plane selected by a system operator at which an image through a ROI is to be generated. The rectangular region 200 defined by gantry angles β1 and β8 and Z-axis locations Z1 and Z3 includes a sub-set of helical data collected during a half scan data acquisition that is to be combined to generate the image corresponding to imaging plane 202. Consistent with half scan principles, the range of rotation between angles β1 and β8 is π+2γ (see again FIG. 3 in this regard).

In FIG. 5, at most gantry angles β the imaging plane 202 is between two row views. For instance, referring specifically to gantry angle βx, at angle βx a row R2 view at Z-axis location Z4 and a row R1 view at Z-axis location Z5 are separated by imaging plane 202. Therefore, at gantry angle βx, a processor can interpolate between the row R2 and R1 views at locations Z4 and Z5 to generate a view within imaging plane 202 corresponding to gantry angle βx. Similar comments are applicable to each gantry angle between angles β2 and β7 as illustrated.

However, between angles β1 and β2, there in only one view for each gantry angle and therefore interpolation is impossible. For instance, at gantry angle βy, row R1 generates a view at Z-axis location Z6 but, clearly, none of the other trajectories within the half scan data segment 200 generate a view at angle βy. Similar comments are applicable to gantry angles between angles β7 and β8 as illustrated. Thus, interpolation is impossible within ranges β1 through β2 and β7 through β8.

Figure 6:
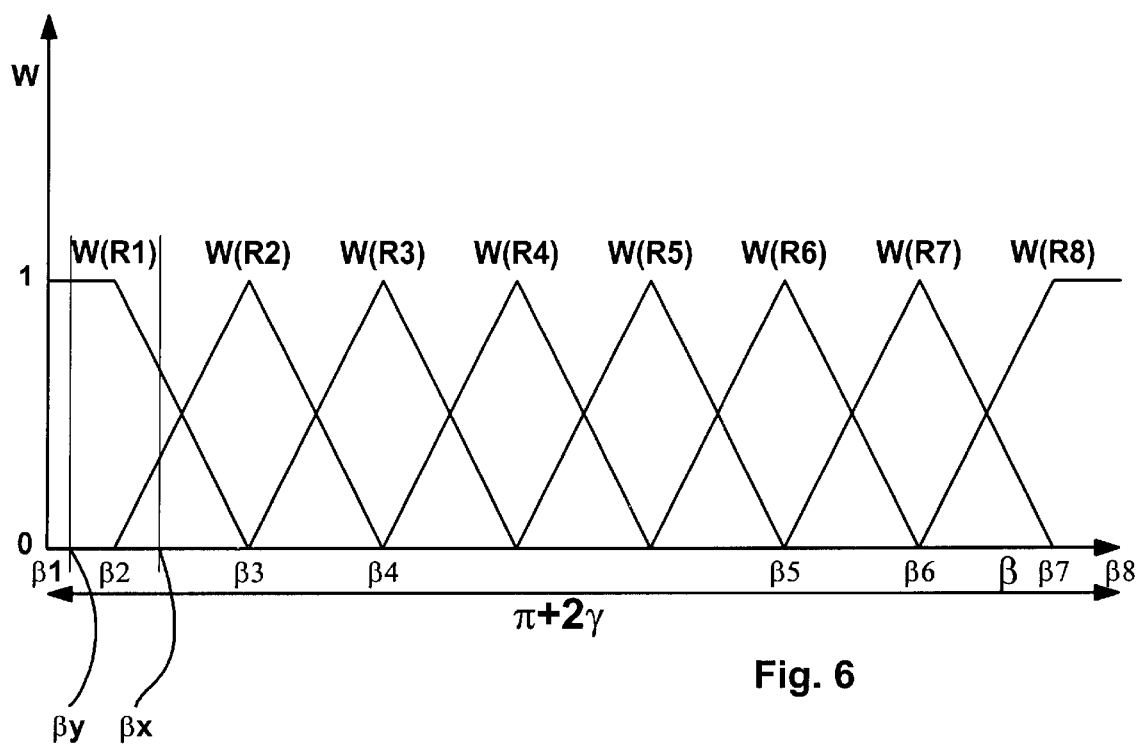
FIG. 6 is a graph illustrating exemplary weighting functions according to the present invention for an eight row CT detector.

Referring now to FIG. 6, exemplary helical weighting functions consistent with the present invention for each row in an eight row detector are illustrated. It can be seen that weighting functions W(R2) through W(R7) corresponding to rows R2 through R7 are identical and conventional. To this end, each function corresponding to rows R2 through R7 is triangular having an apex value of one and tapering off linearly to either side as gantry angle β increases and decreases. More specifically, referring to weighting function W(R2) and referring also to FIG. 5, at gantry angle β3, the view trajectory defined by row R2 is aligned with imaging plane 202 and therefore the row weighting function W(R2) has an apex at angle β3 and tapers off to either side from there. In addition, the width of each weighting function W(R2) through W(R7) is equal to the dimension 204 (see FIG. 4) between the central points of adjacent detector rows. Therefore, for example, weighting function W(R2) is applied between gantry angles β2 and β4, weighting function W(R7) is applied between gantry angles β5 and β7 and so on.

Referring still to FIG. 6, weighting function W(R1) corresponding to row R1 is different than the weighting functions corresponding to center (i.e., non-end) detector rows. To this end, referring also to FIG. 5, between gantry angles β2 and β3 where row R2 generates views that can be interpolated with views from row R1 to identify data corresponding to imaging plane 202, weighting function W(R1) is essentially identical to the weighting functions W(R2) through W(R7). However, between gantry angles β1 and β2, weighting function W(R1) has a value of one. Similarly, between gantry angles β6 and β7 where row R7 generates views that can be interpolated with views from row R8 to identify data corresponding to imaging plane 202, weighting function W(R8) is essentially identical to the weighting functions W(R2) through W(R7). However, between gantry angles β7 and β8, weighting function W(R8) has a value of one.

The weighting functions illustrated in FIG. 6 can be expressed as a series of equations. To this end, if the number of detector rows is denoted as N, the weighting functions can be expressed as, for rows Rr where 1<r<N:

$$w_r = \begin{cases} 1 + \dfrac{\beta - \beta_r}{\beta_P}, & \beta_r - \beta_P \le \beta < \beta_r \\ 1 - \dfrac{\beta - \beta_r}{\beta_P}, & \beta_r + \beta_P > \beta \ge \beta_r \\ 0, & \text{otherwise} \end{cases} \qquad \text{Eq. 2}$$

where $$\beta_P = \frac{2\pi}{p}$$

and $$\beta_r = r\beta_P.$$

Assuming that $\beta_1-\beta_p=0$, for row R1:

$$w_1 = \begin{cases} 1, & \beta_0 \le \beta < \beta_1 \\ 1 - \dfrac{\beta - \beta_1}{\beta_P}, & \beta_1 + \beta_P > \beta \ge \beta_1 \\ 0, & \text{otherwise} \end{cases} \quad \text{Eq. 3}$$

where $\beta_0$ corresponds to the beginning view angle of a half scan image (e.g., $\beta_1$ in FIG. 5). For row RN:

$$w_N = \begin{cases} 1 + \dfrac{\beta - \beta_N}{\beta_P}, & \beta_N - \beta_P \le \beta < \beta_N \\ 1, & \beta_N \le \beta < \beta_{N+1} \\ 0, & \text{otherwise} \end{cases} \quad \text{Eq. 4}$$

where $\beta$ is the gantry fan angle, $\beta_{N+1}$ corresponds to the ending view angle of the half scan image (e.g., $\beta_8$ in FIG. 5).

Thus, consistent with other helical weighting schemes, the summation of weighting functions for all detector rows at each gantry angle $\beta$ satisfies the following equation:

$$\sum_{r=1}^{N} w_r = 1 \quad \text{Eq. 5}$$

It should be understood that the methods and apparatuses described above are only exemplary and do not limit the scope of the invention, and that various modifications could be made by those skilled in the art that would fall under the scope of the invention.

To apprise the public of the scope of this invention, the following claims are made:

What is claimed is:

1. An apparatus for use with a CT imaging system including a radiation source and opposed detector mounted to a gantry on opposite sides of an imaging area, the detector including N separate detector rows arranged perpendicular to a translation axis, the apparatus for producing a tomographic slice image through a slice image plane passing through a region of interest (ROI) within an object from a projection data set acquired in a helical scan having a pitch p where the data set includes N separate row data sets corresponding to the N detector rows and each row data set correlates row views with gantry angles, a central angle $\beta$ within the projection data set essentially aligned with the slice image plane, the apparatus comprising an image reconstructor configured to:

create a separate projection data array for each of the N separate row data sets;

apply a helical weighting function to each of the projection data arrays to generate a separate helical weighted array for each projection data array, the weighting function to be applied to each projection data array being, for rows where 1<r<N:

$$w_r = \begin{cases} 1 + \dfrac{\beta - \beta_r}{\beta_P}, & \beta_r - \beta_P \le \beta < \beta_r \\ 1 - \dfrac{\beta - \beta_r}{\beta_P}, & \beta_r + \beta_P > \beta \ge \beta_r \\ 0, & \text{otherwise} \end{cases}$$

where $$\beta_P = \dfrac{2\pi}{p},$$

and $\beta_r = r\beta_p$;

for the first detector row in the detector:

$$w_1 = \begin{cases} 1, & \beta_0 \le \beta < \beta_1 \\ 1 - \dfrac{\beta - \beta_1}{\beta_P}, & \beta_1 + \beta_P > \beta \ge \beta_1 \\ 0, & \text{otherwise} \end{cases}$$

and, for the Nth detector row in the detector:

$$w_N = \begin{cases} 1 + \dfrac{\beta - \beta_N}{\beta_P}, & \beta_N - \beta_P \le \beta < \beta_N \\ 1, & \beta_N \le \beta < \beta_{N+1} \\ 0, & \text{otherwise} \end{cases}$$

where $\beta$ is a gantry angle, $\beta_0$ corresponds to the beginning view angle of a half scan image, $\beta_{N+1}$ corresponds to the ending view angle of the half scan image and $\beta_1-\beta_p=0$.

2. The apparatus of claim 1 wherein the reconstructor is further configured to apply a half scan weighted function to each of the helical weighted arrays thereby generating a half scan weighted array for each helical weighted array and wherein the reconstructor is configured to construct the slice image using the half scan weighted arrays.

3. The apparatus of claim 2 wherein the reconstructor is configured to use the half scan weighted arrays to generate the slice image by, for each gantry angle within the slice image plane, adding the half scan weighted arrays corresponding to each detector row and to the gantry angle to generate a combined weighted array for the angle, filtering the combined weighted arrays and then back-projecting the combined weighted arrays.

4. The apparatus of claim 2 wherein the reconstructor is configured to use the half scan weighted arrays to generate the slice image by, for the half scan weighted arrays corresponding to each detector row, filtering and back-projecting the half scan gated arrays to generate a row specific slice image and then adding the row specific slice images to generate a final slice image within the image plane.

5. The apparatus of claim 1 wherein the reconstructor is further configured to, prior to applying the helical weighting function to each of the projection data arrays, storing the data arrays in a system memory for reconstructing a plurality of slice images.

6. An apparatus for use with a CT imaging system including a radiation source and opposed detector mounted to a gantry on opposite sides of an imaging area, the source generating a fan beam including rays at varying fan beam angles $\gamma$, the detector including N separate detector rows arranged perpendicular to a translation axis, the apparatus for producing a tomographic slice image through a slice image plane passing through a region of interest (ROI) within an object from a projection data set acquired in a helical scan having a pitch p where the data set includes N separate row data sets corresponding to the N detector rows where first and last detector rows are row R1 and row RN and there are N-2 rows between rows R1 and RN and each row data set correlates row views with gantry angles, a central angle β within the projection data set essentially aligned with the slice image plane, the apparatus comprising an image reconstructor configured to:

create a separate projection data array for each of the N separate row data sets;

apply a first helical weighting function to each of the projection data arrays corresponding to the N-2 rows between row R1 and row RN to generate a separate helical weighted array for each of the N-2 rows apply a second helical weighting function to the projection data array corresponding to row R1 to generate a separate helical weighted array for row R1;

apply a third helical weighting function to the projection data array corresponding to row RN to generate a separate helical weighted array for row RN; and construct a slice image using the helical weighted arrays corresponding to rows 0 through N.

7. The apparatus of claim 6 wherein the weighting function corresponding to row R1 is applied between a first gantry angle β1 and a third gantry angle β3 and the weighting function corresponding to the detector row adjacent row R1 is applied between a second gantry angle β2 and a fourth gantry angle β4 where second gantry angle β2 is prior to third gantry angle β3 and wherein the second weighting function is one between the first and second gantry angles.

8. The apparatus of claim 7 wherein the weighting function corresponding to row RN-1 is applied between a fifth gantry angle β5 and a seventh gantry angle β7 and the weighting function corresponding to row RN is applied between a sixth gantry angle β6 and an eighth gantry angle β8 where sixth gantry angle β6 is prior to seventh gantry angle β7 and wherein the third weighting function is one between the seventh and eighth gantry angles.

9. The apparatus of claim 8 wherein the weighting functions for each of the N-2 rows between row R1 and row RN are triangular, each having an apex aligned with a selected imaging plane where the weight value is one and each tapering off to zero on either side thereof.

10. The apparatus of claim 9 wherein each weighting function is applied across a gantry angle range corresponding to the Z-axis distance between the centers of adjacent detector rows.

11. A method for use with a CT imaging system including a radiation source and opposed detector mounted to a gantry on opposite sides of an imaging area, the detector including N separate detector rows arranged perpendicular to a translation axis, the method for producing a tomographic slice image through a slice image plane passing through a region of interest (ROI) within an object from a projection data set acquired in a helical scan having a pitch p where the data set includes N separate row data sets corresponding to the N detector rows and each row data set correlates row views with gantry angles, a central angle β within the projection data set essentially aligned with the slice image plane, the method comprising the steps of:

creating a separate projection data array for each of the N separate row data sets;

applying a helical weighting function to each of the projection data arrays to generate a separate helical weighted array for each projection data array, the weighting function to be applied to each projection data array being, for rows r where 1<r<N:

$$w_r = \begin{cases} 1 + \dfrac{\beta - \beta_r}{\beta_P}, & \beta_r - \beta_P \le \beta < \beta_r \\ 1 - \dfrac{\beta - \beta_r}{\beta_P}, & \beta_r + \beta_P > \beta \ge \beta_r \\ 0, & \text{otherwise} \end{cases}$$

where $$\beta_P = \frac{2\pi}{p},$$

and $\beta_r = r\beta_p;$ for the first detector row in the detector:

$$w_1 = \begin{cases} 1, & \beta_0 \le \beta < \beta_1 \\ 1 - \dfrac{\beta - \beta_1}{\beta_P} & \beta_1 + \beta_P > \beta \ge \beta_1 \\ 0, & \text{otherwise} \end{cases}$$

and, for the Nth detector row in the detector:

$$w_N = \begin{cases} 1 + \dfrac{\beta - \beta_N}{\beta_P}, & \beta_N - \beta_P \le \beta < \beta_N \\ 1, & \beta_N \le \beta_{N+1} \\ 0, & \text{otherwise} \end{cases}$$

where β is a gantry angle, $\beta_0$ corresponds to the beginning view angle of a half scan image, $\beta_{N+1}$ corresponds to the ending view angle of the half scan image and $\beta_1 - \beta_p = 0$.

12. The method of claim 11 further including the step of applying a half scan weighted function to each of the helical weighted arrays thereby generating a half scan weighted array for each helical weighted array and constructing the slice image using the half scan weighted arrays.

13. The method of claim 12 wherein the step of constructing includes, for each gantry angle within the slice image plane, adding the half scan weighted arrays corresponding to each detector row and to the gantry angle to generate a combined weighted array for the angle, filtering the combined weighted arrays and then back-projecting the combined weighted arrays.

14. The method of claim 12 wherein the step of constructing includes, for the half scan weighted arrays corresponding to each detector row, filtering and back-projecting the half scan gated arrays to generate a row specific slice image and then adding the row specific slice images to generate a final slice image within the image plane.

15. The method of claim 11 further including the step of, prior to applying the helical weighting function to each of the projection data arrays, storing the data arrays in a system memory for reconstructing a plurality of slice images.

16. A method for use with a CT imaging system including a radiation source and opposed detector mounted to a gantry on opposite sides of an imaging area, the source generating a fan beam including rays at varying fan beam angles γ, the detector including N separate detector rows arranged perpendicular to a translation axis, the method for producing a tomographic slice image through a slice image plane passing through a region of interest (ROI) within an object from a projection data set acquired in a helical scan having a pitch p where the data set includes N separate row data sets corresponding to the N detector rows where first and last detector rows are row R1 and row RN and there are N-2 rows between rows R1 and RN and each row data set correlates row views with gantry angles, a central angle β within the projection data set essentially aligned with the slice image plane, the method comprising the steps of:

creating a separate projection data array for each of the N separate row data sets;

applying a first helical weighting function to each of the projection data arrays corresponding to the N-2 rows between row 0 and row N to generate a separate helical weighted array for each of the N-2 rows applying a second helical weighting function to the projection data array corresponding to row R1 to generate a separate helical weighted array for row R1;

applying a third helical weighting function to the projection data array corresponding to row RN to generate a separate helical weighted array for row RN; and constructing a slice image using the helical weighted arrays corresponding to rows R1 through RN.

17. The method of claim 16 wherein the weighting function corresponding to row R1 is applied between a first gantry angle β1 and a third gantry angle β3 and the weighting function corresponding to the detector row adjacent row R1 is applied between a second gantry angle β2 and a fourth gantry angle β4 where second gantry angle β2 is prior to third gantry angle β3 and wherein the second weighting function is one between the first and second gantry angles.

18. The method of claim 17 wherein the weighting function corresponding to row RN-1 is applied between a fifth gantry angle β5 and a seventh gantry angle β7 and the weighting function corresponding to row RN is applied between a sixth gantry angle β6 and an eighth gantry angle β8 where sixth gantry angle β6 is prior to seventh gantry angle β7 and wherein the third weighting function is one between the seventh and eighth gantry angles.

19. The method of claim 18 wherein the weighting functions for each of the N-2 rows between row R1 and row RN are triangular, each having an apex aligned with a selected imaging plane where the weight value is one and each tapering off to zero on either side thereof.

20. The method of claim 19 wherein each weighting function is applied across a gantry angle range corresponding to the Z-axis distance between the centers of adjacent detector rows.

* * * * *